(12) United States Patent
Sano et al.

(10) Patent No.: US 6,712,760 B2
(45) Date of Patent: *Mar. 30, 2004

(54) TELEVISION DEVICE OF PORTABLE ENDOSCOPE

(75) Inventors: Hiroshi Sano, Chiba (JP); Kenichi Ohara, Gunma (JP); Masaaki Nakashima, Saitama (JP); Yoshihiro Obata, Saitama (JP)

(73) Assignee: PENTAX Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/827,912

(22) Filed: Apr. 9, 2001

(65) Prior Publication Data

US 2002/0022763 A1 Feb. 21, 2002

(30) Foreign Application Priority Data

Apr. 10, 2000 (JP) .................... P.2000-107419
Apr. 10, 2000 (JP) .................... P.2000-107420
Apr. 10, 2000 (JP) .................... P.2000-107421

(51) Int. Cl.[7] ................................. A61B 1/04
(52) U.S. Cl. .................... 600/160; 600/178; 600/179; 348/68; 348/73
(58) Field of Search ............... 600/109, 110, 600/127, 160, 170, 171, 172, 173, 175, 179, 178; 348/65, 68, 73

(56) References Cited

U.S. PATENT DOCUMENTS

| | | | | |
|---|---|---|---|---|
| 4,281,910 A | * | 8/1981 | Takayama | 348/73 |
| 4,633,304 A | * | 12/1986 | Nagasaki | 128/903 |
| 5,745,165 A | | 4/1998 | Atsuta et al. | |
| 5,877,802 A | | 3/1999 | Takahashi et al. | |
| 5,879,289 A | * | 3/1999 | Yarush et al. | 600/109 |
| 6,095,970 A | * | 8/2000 | Hidaka et al. | 600/109 |
| 6,117,071 A | | 9/2000 | Ito et al. | |

FOREIGN PATENT DOCUMENTS

| | | | | |
|---|---|---|---|---|
| EP | 0774231 | | 5/1997 | |
| JP | 60-88921 | * | 5/1985 | A61B/1/00 |
| JP | 8-150114 | | 6/1996 | |
| JP | 9-292575 | * | 11/1997 | G02B/23/24 |
| JP | 10-165362 | * | 6/1998 | A61B/1/04 |
| JP | 11211997 | | 8/1999 | |

* cited by examiner

Primary Examiner—John Mulcahy
(74) Attorney, Agent, or Firm—Greenblum & Bernstein, P.L.C.

(57) ABSTRACT

A television device of a portable endoscope includes an endoscope including an inserted portion and an operating portion coupled to a base end of the inserted portion, a light source for lightening a subject through the inserted portion provided in the endoscope, a radio transmission television camera for obtaining an image of the subject through the inserted portion and radioing the image as the video signal provided in the endoscope, and a power source, which supplies a power for the light source and the radio transmission television camera, provided in the operating portion.

24 Claims, 11 Drawing Sheets

TELEVISION DEVICE OF PORTABLE ENDOSCOPE

BACKGROUND OF THE INVENTION

1. Technical Field of the Invention

The present invention relates to a television device of a portable endoscope in which a light source unit including a light source lamp and its power supply is directly coupled to an operating portion.

2. Related Art

In a portable endoscope, generally, an eyepiece portion for observing an endoscopic observation picture and an incident end portion of a light guide for lighting are placed at an operating portion coupled to a base end of an inserted portion, and a light source unit including a light source lamp for supplying the illumination light to the light guide and a power source for turning on its light source lamp is provided so as to be directly coupled to the operating portion.

In order to project the picture observed with such the portable endoscope on a television monitor, hitherto, a television camera is mounted to the eyepiece portion of the portable endoscope and a video signal obtained by its television camera is transmitted to a control unit by a signal cable.

The portable endoscope in which any codes such as a light guide code and the like are not extended out of the operating portion produces the best operational efficiency and facilitation of cleaning and disinfection after use. However, in case that the television camera is mounted to the portable endoscope, the signal cable extending out of its television camera obstructs the operational efficiency greatly.

SUMMARY OF THE INVENTION

Therefore, an object of the invention is to provide a television device of a portable endoscope which can take an endoscopic observation picture in a state where a good operational efficiency of the portable endoscope is kept.

To achieve the above object, according to a first aspect of the invention, television device of a portable endoscope comprising:

an endoscope including an inserted portion and an operating portion coupled to a base end of the inserted portion;

a light source for lightening a subject through the inserted portion provided in the endoscope;

a radio transmission television camera for obtaining an image of the subject through the inserted portion and radioing the image as the video signal provided in the endoscope; and a power source which is provided in the operating portion and supplies a power for the light source and the radio transmission television camera.

According to a second aspect, in the television device of the portable endoscope of the first aspect, the radio transmission television camera is detachably coupled to the operating portion.

According to a third aspect, in the television device of the portable endoscope of the second aspect, an eyepiece portion, through which the image of the subject is projected and to which the radio transmission camera is coupled, is provided at the operation portion.

According to a forth aspect, in the television device of the portable endoscope of the third aspect, a wire for electrically connecting the radio transmission television camera to the power source is provided in the operating portion and the eyepiece portion.

According to a fifth aspect, in the television device of the portable endoscope of the third aspect, a wire for electrically connecting the radio transmission television camera unit to the power source is placed outside the operating portion and the eyepiece portion.

According to a sixth aspect, in the television device of the portable endoscope of the first aspect, a light source unit including the light source and the power source is detachably coupled to the operating portion.

According to a seventh aspect, in the television device of the portable endoscope of the first aspect, the radio transmission television camera includes a solid image sensor for capturing an image of the subject and a circuit including at least one of a drive circuit for driving the solid image sensor, a process circuit for processing the video signal and a transmitting circuit for transmitting the video signal.

According to an eight aspect, in the television device of the portable endoscope of the seventh aspect, the solid image sensor and the circuit are integrally formed.

According ninth aspect, in the television device of the portable endoscope of the seventh aspect, the solid image sensor is provided in a distal end portion of the inserted portion.

According to an tenth aspect, in the television device of the portable endoscope of the seventh aspect, the solid image sensor and the light source is provided in a distal end body detachably mounted to a distal end of the inserted portion.

According to an eleventh aspect, in the television device of the portable endoscope of the tenth aspect, the distal end body including the solid image sensor and the light source is exchangeable for another type of distal end body for obtaining the image of the subject in different direction.

According to a twelfth aspect, in the television device of the portable endoscope of the first aspect, the power source is detachably provided in the operating portion.

According to a thirteenth aspect, in the television device of the portable endoscope of the first aspect, the video signal is transmitted by using infrared rays or radio waves.

According to a fourteenth aspect, in the television device of the portable endoscope of the first aspect, a transmitting antenna is provided at the operating portion.

According to a fifteenth aspect, in the television device of the portable endoscope of the first aspect, the power source is a power electric cell.

The present disclosure relates to the subject matter contained in Japanese patent application Nos. 2000-107419 (filed on Apr. 10, 2000), 2000-107420 (filed on Apr. 10, 2000), and 2000-107421 (filed on Apr. 10, 2000), which are expressly incorporated herein by reference in their entireties.

DESCRIPTION OF THE PREFERRED EMBODIMENT

Modes for carrying out the invention will be described with reference to drawings.

First Embodiment

Figure 2:
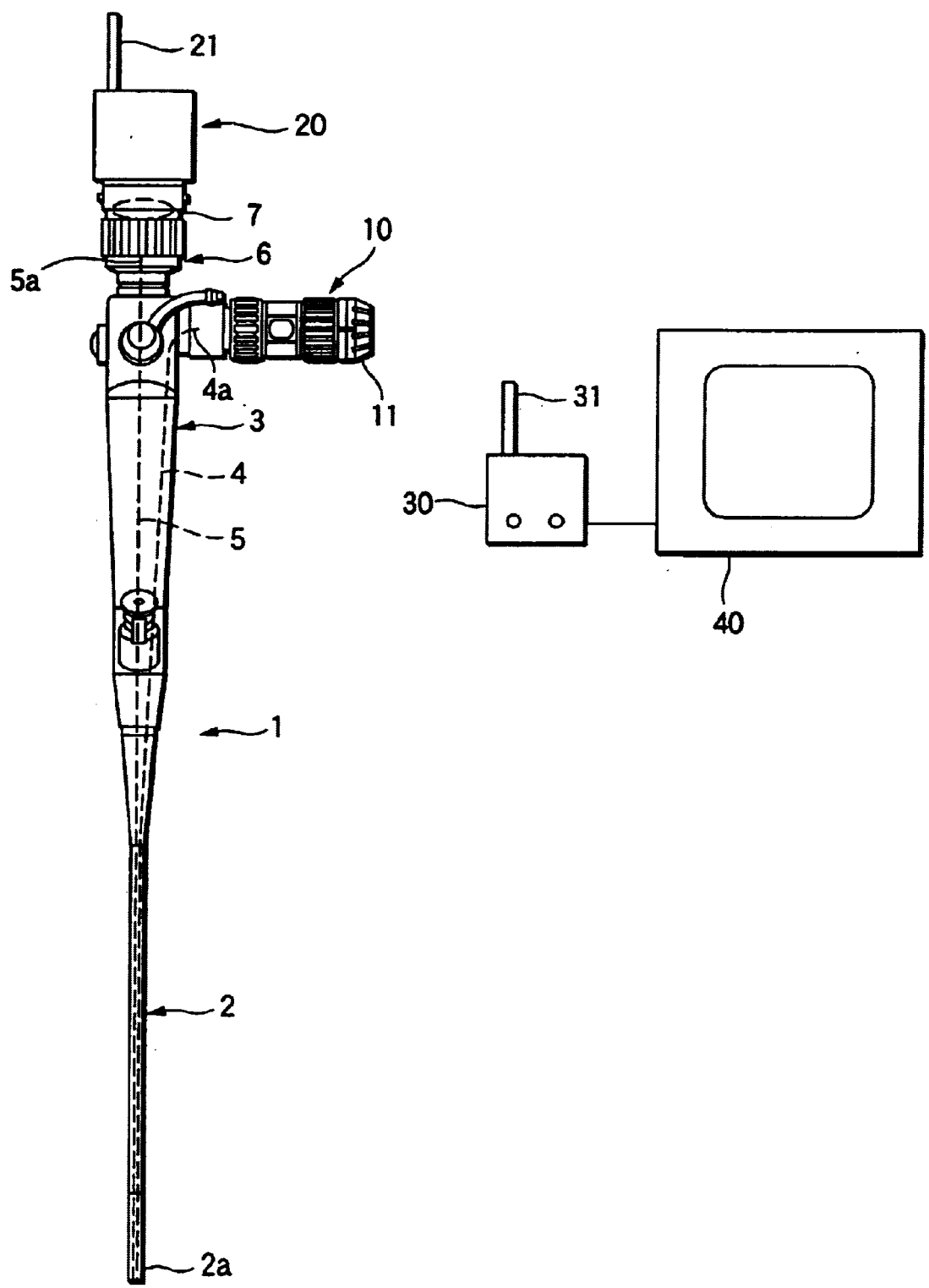
FIG. 2 is an external front view showing the whole structure of the portable endoscope and the television device according to the first embodiment of the invention.

FIG. 2 shows a first embodiment of a portable endoscope and a television device according to the invention.

An inserted portion 2 of a portable endoscope 1 is covered with a flexible tube. An incident end portion 4a of a light guide fiber bundle for lighting 4 is placed at an operating portion 3 coupled to a base end of the inserted portion 2.

An eyepiece portion 6 for observing an endoscopic observation picture transmitted by an image guide fiber bundle 5 is projectingly provided at the upper end portion of the operating portion 3. An image projecting end surface of the image guide fiber bundle 5 can be observed by being enlarged by an eyepiece lens 7. Reference numeral 5a is a projection end of the image guide fiber bundle 5.

A radio transmission television camera 20 is detachably coupled to the eyepiece portion 6, which obtains the endoscopic observation picture, the picture on the image projecting end surface of the image guide fiber bundle 5, projected through the eyepiece lens 7 and transmits its video signal by radio. Its coupling is performed by well-known bayonet mechanism or the like. Reference numeral 21 is a transmitting antenna.

The incident end portion of the image guide fiber bundle 5 is placed in an imaging position of a subject by an objective optical system (not shown) included in a distal end portion 2a of the inserted portion 2. A projection end of the light guide fiber bundle 4 is placed so as to lighten its subject.

A light source unit 10 for supplying the illumination light to the light guide fiber bundle 4 is directly detachably coupled to the upper portion of a side surface of the operating portion 3. Reference numeral 11 is a switch ring for performing ON/OFF operation of the light source unit 10.

Figure 1:
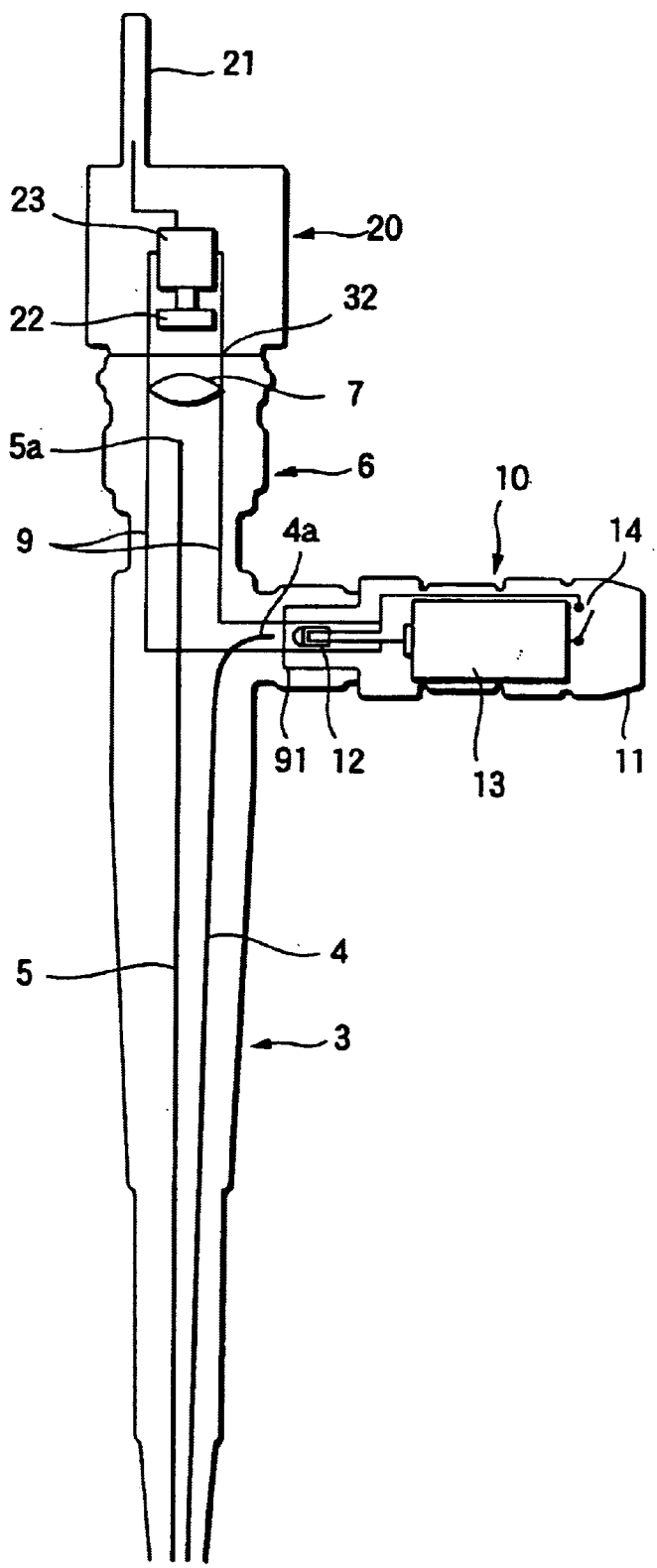
FIG. 1 is a schematic diagram showing the inside structure of a portable endoscope and a television device according to a first embodiment of the invention.

In the light source unit 10, a light source lamp 12 constituted by a so-called miniature lamp or the like is placed in a position facing to the incident end surface of the light guide fiber bundle 4, as shown in FIG. 1.

A power electric cell 13 for supplying electric power to the light source lamp 12 is exchangeably included in the light source unit 10. A switch 14 for connecting/cutting electric conduction between the light source lamp 12 and the power electric cell 13 is opened and closed by the switch ring 11.

In the radio transmission television camera 20, an image receptor surface of a solid image sensor 22 is placed in a projection position of the image projecting end surface of the image guide fiber bundle 5. A drive circuit for driving the solid image sensor 22, a process circuit for processing the video signal, a video signal transmitting circuit, and the like are mounted on a circuit substrate 23 to which the solid image sensor 22 is attached.

An image sensor scan timing circuit, a video signal generating circuit and the like may be integrated on the same chip as the solid image sensor 22, a synchronous signal generating circuit. In case that a sensor of, for example, CMOS structure is used as the solid image sensor 22, such the integration can be readily performed.

One or plural circuits of various circuits such as an auto white balance circuit, either a lamp lighting timing output circuit for regulating the lightness of the picture by the lighting time of the light source lamp 12 or an electronic shutter circuit for regulating the lightness of the picture by changing the storage time of the image signal, an A/D (analog/digital) conversion circuit, a D/A (digital/analog) conversion circuit, and the like may be included in the same chip as the solid image sensor 22.

Figure 3:
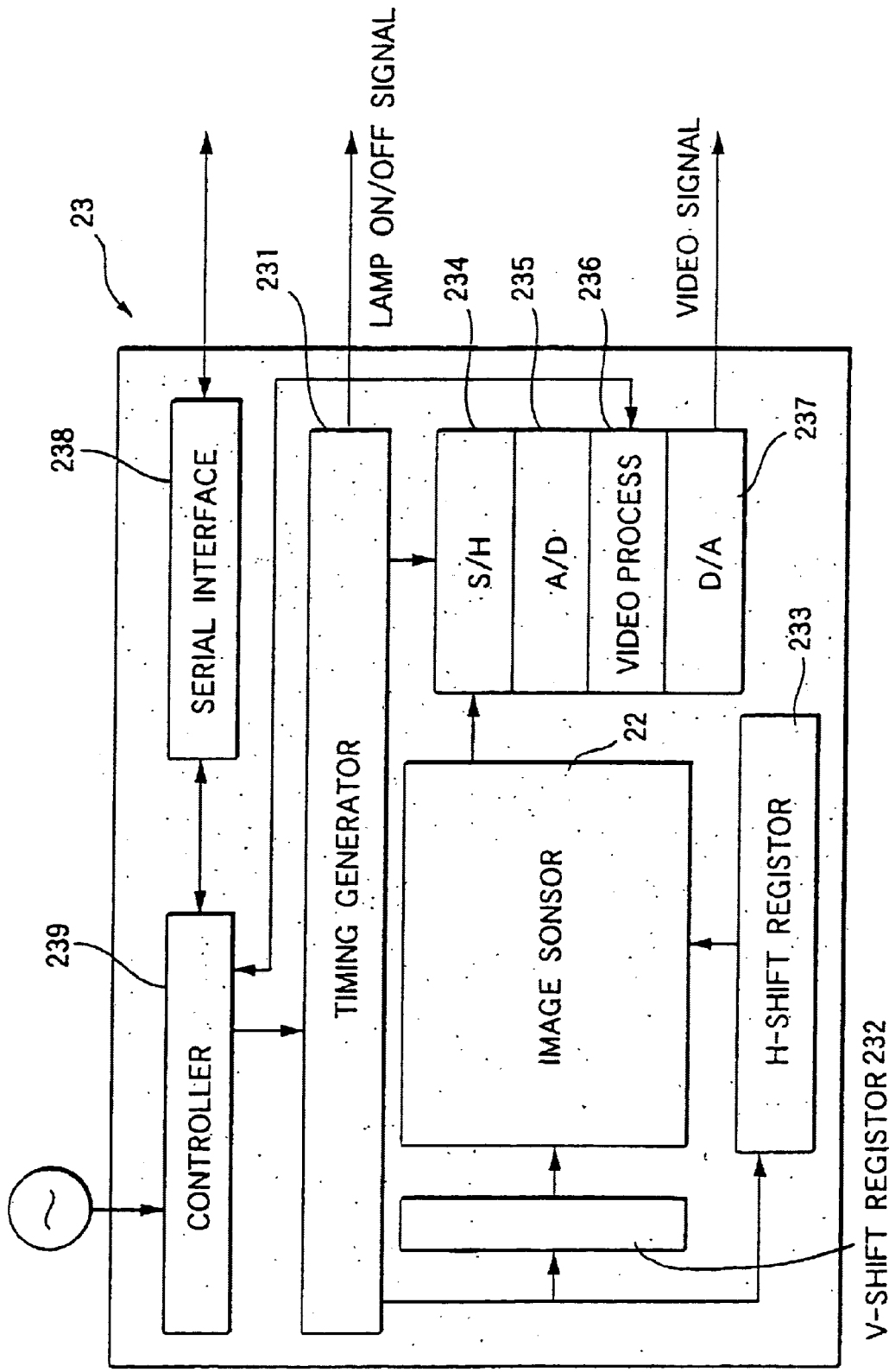
FIG. 3 is a block diagram showing one example in which various circuits is integrated on a circuit substrate to which a solid image sensor is mounted.

FIG. 3 shows one example of the circuit substrate 23 in which such the integration is performed. On the circuit substrate 23 to which the solid image sensor 22 has been attached, there are provided a timing generator 231 for sending out synchronous signals, a shift register 232 for performing vertical scanning of the solid image sensor 22, a shift register 233 for performing horizontal scanning of the solid image sensor 22, a sample hold (S/H) circuit 234, an A/D conversion circuit 235, a D/A conversion circuit 237, and a video process circuit 236 for performing video signal processing.

Figure 4:
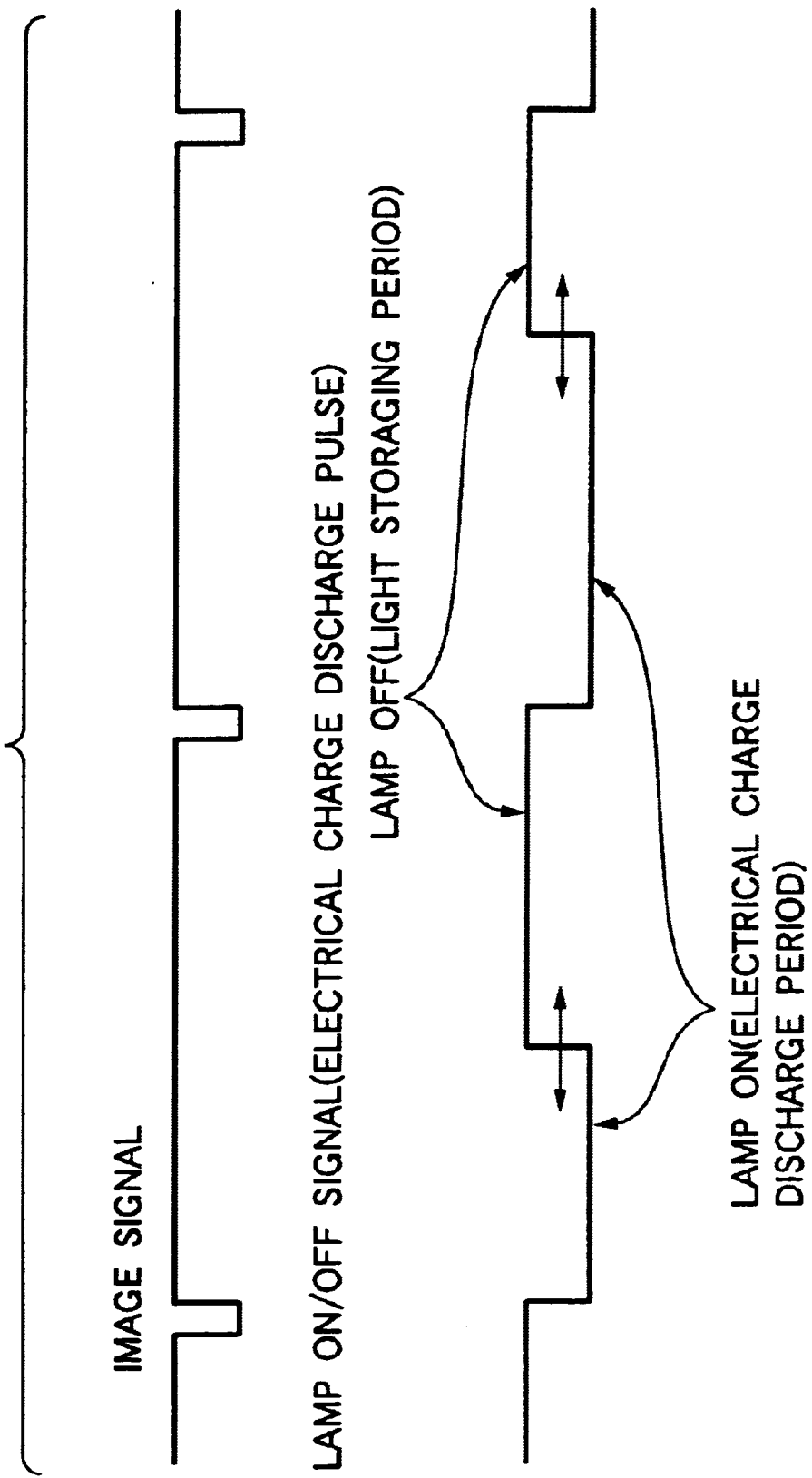
FIG. 4 is a time chart showing the lighting control state of a light source lamp in the circuit shown in FIG. 3.

The circuit substrate 23 includes a serial interface 238 that inputs and outputs adjustment signals for adjusting the state of the picture between an external circuit and it, and a controller 239 that detects the video signal and controls the lighting time of the light source lamp 12 so that the picture has the proper lightness, for example, as shown in a time chart of FIG. 4.

Figure 5:
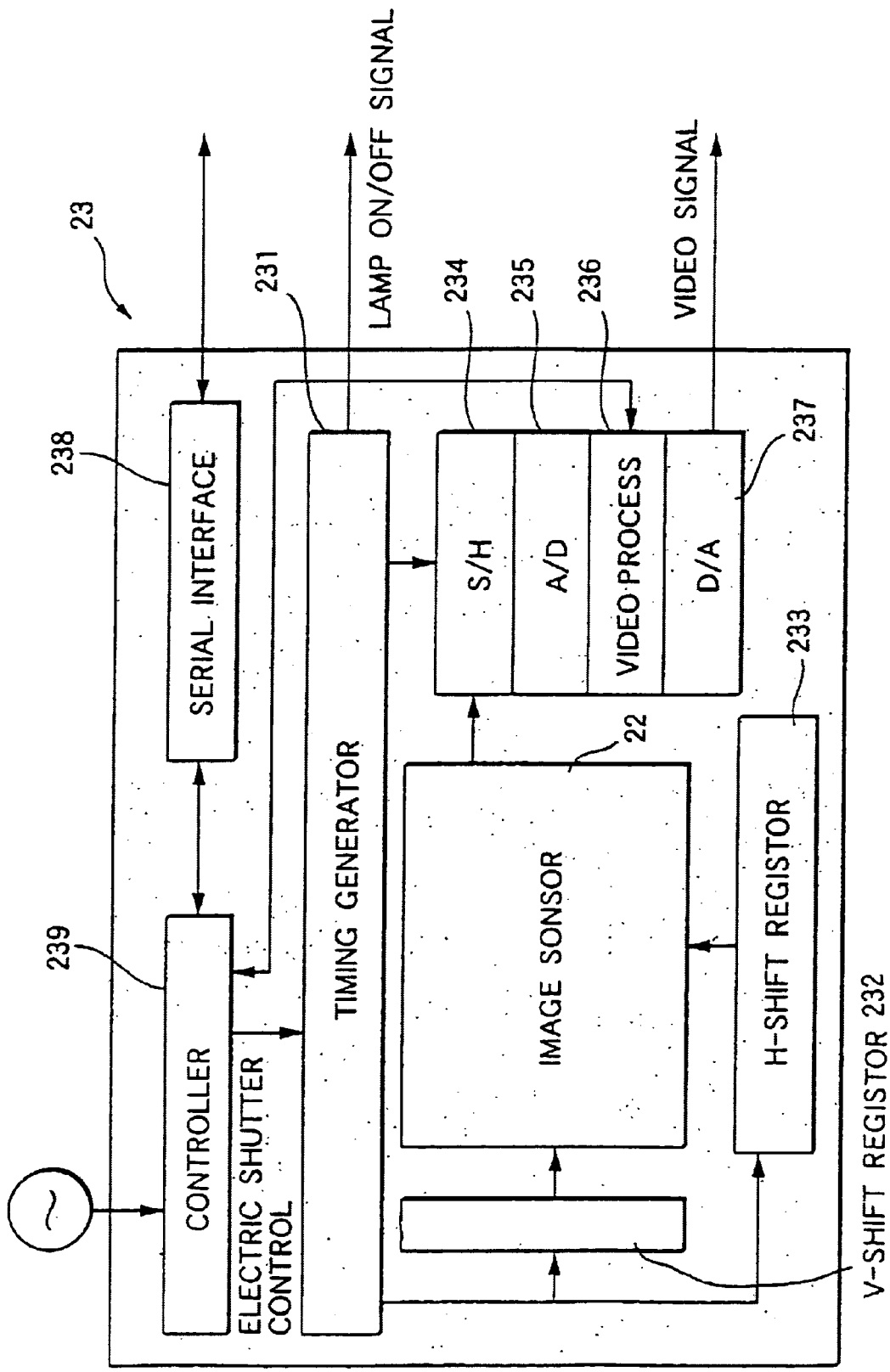
FIG. 5 is a block diagram showing a second example in which various circuits is integrated on a circuit substrate to which a solid image sensor is mounted.

FIG. 5 shows the circuit substrate 23 in which the lightness of the picture is controlled not by the lighting time of the light source lamp 12 but by the storage time of the image signal into the solid image sensor 22 using an electric shutter (not shown) placed in the position where the incident light to the solid image sensor 22 passes. The controller 239 outputs a signal for controlling the opening and closing time of the electric shutter. According to its signal, the electric shutter opens only for the lamp ON period shown in FIG. 4.

Turning to FIG. 1, the power for driving the circuits 22, 23 in the radio transmission television camera 20 is supplied from the power electric cell 13 in the light source unit 10 through an electric wire 9 wired in the operating portion 3 and the eyepiece portion 6 to the circuit substrate 23.

Contacts 91 and 92 are provided respectively for a joint portion of the light source unit 10 in relation to the operating portion 3 and a joint portion of the radio transmission television camera 20 in relation to the eyepiece portion 6. When the light source unit 10 is coupled to the operating portion 3, the power electric cell 13 and the electric wire 9 are electrically connected to each other through the switch 14; and when the radio transmission television camera 20 is coupled to the eyepiece portion 6, the electric wire 9 and the circuit substrate 23 are electrically connected to each other.

As a result, by turning and operating the switch ring 11 to close the switch 14, the light source lamp 12 is turned on and simultaneously the power for operating the radio transmission television camera 20 is supplied all from the power electric cell 13 of the light source unit 10. Further, any cables are not extended out of the radio transmission television camera 20 and the operating portion 3, and the endoscopic observation picture is taken by the radio transmission television camera 20 to transmit its video signal from the transmitting antenna 21 by radio.

Radio wave of the video signal thus transmitted from the transmitting antenna 21, as shown in FIG. 2, is received by a receiver 30 provided with a receiving antenna 31, and the endoscopic observation picture is projected onto a television monitor 40 connected to its receiver 30.

Figure 6:
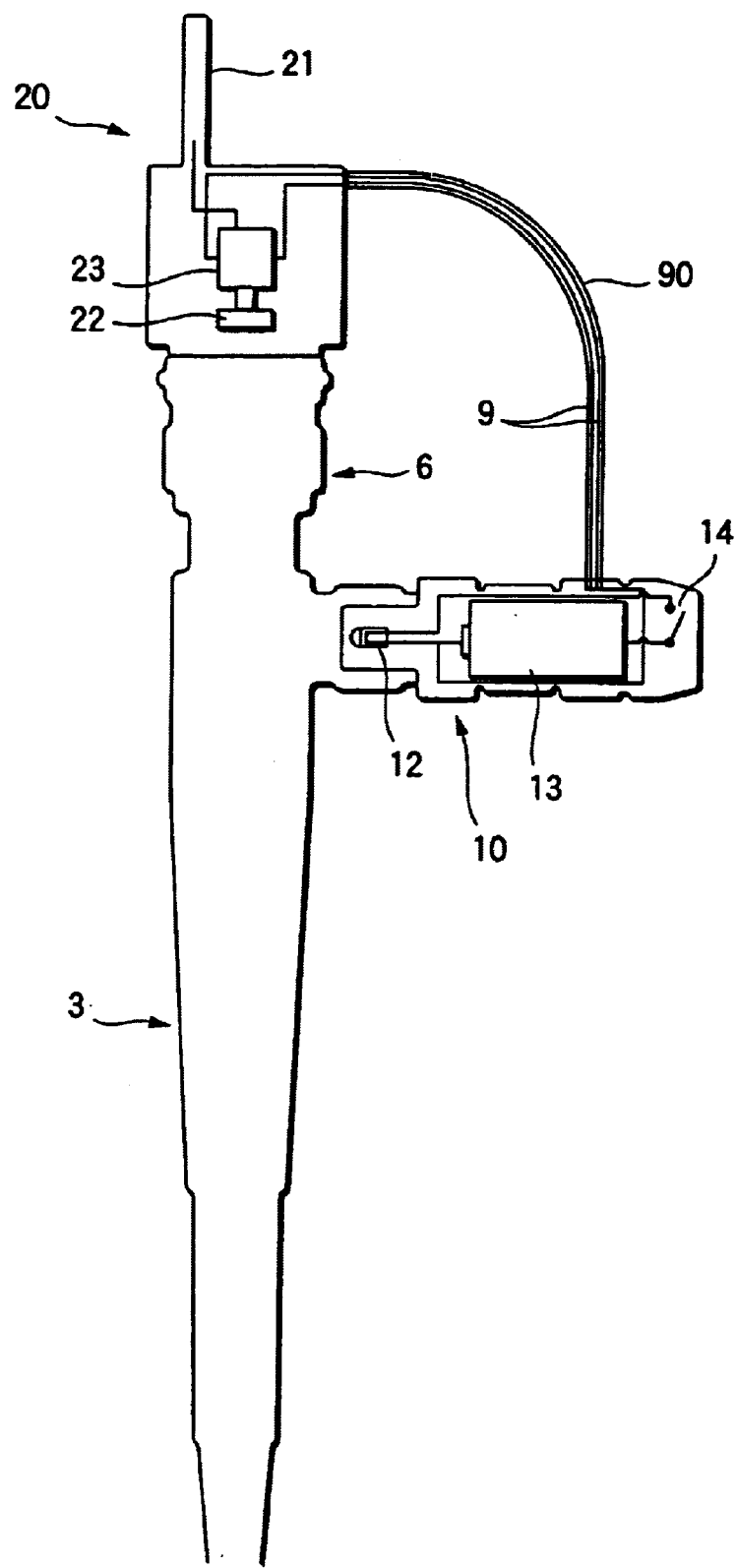
FIG. 6 is a schematic diagram showing modification of the first embodiment of the invention.

The invention is not limited to the above embodiment. For example, as shown in FIG. 6, a connection cable 90 in which the electric wire 9 for directly connecting the light source unit 10 to the radio transmission television camera 20 is inserted may be placed outside the eyepiece portion 6 and the operating portion 3.

In this case, it is desirable that the connection cable 90 is constituted connectably and separably in relation to both the light source unit 10 and the radio transmission television camera 20, or in relation to the light source unit 10.

Second Embodiment

Figure 7:
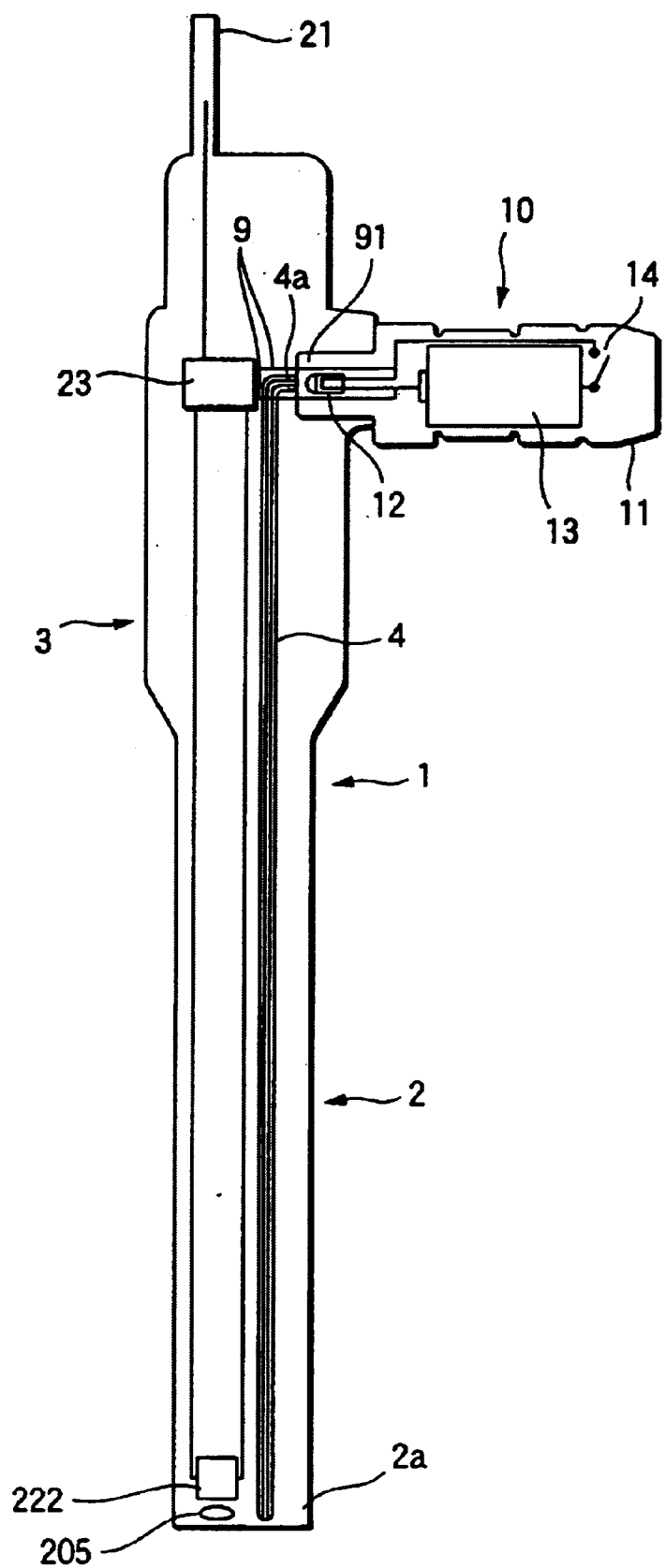
FIG. 7 is a schematic diagram showing the inside structure of a portable endoscope according to a second embodiment of the invention.
Figure 8:
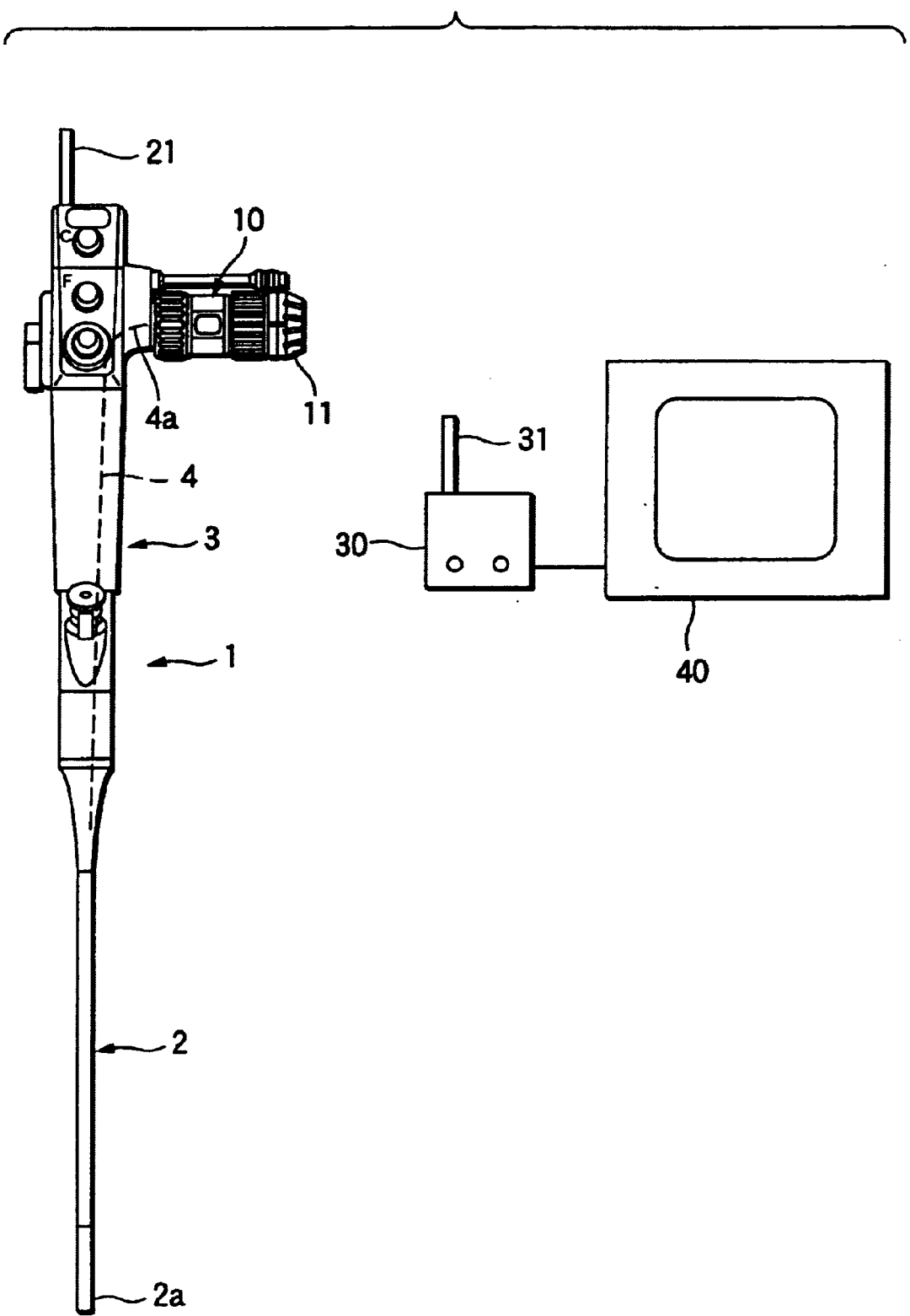
FIG. 8 is an external front view of the portable endoscope according to the second embodiment of the invention.

FIGS. 7 and 8 show a second embodiment of a portable endoscope according to the invention. Since the same component parts as those in the first embodiment are denoted by the same reference numerals, their detailed description is omitted.

The difference between the first embodiment and the second embodiment is that an objective optical system 205 is included in a distal end portion 2*a* of an inserted portion 2, and an image surface of a slid image sensor 222 is placed in an imaging position of a subject by its objective optical 205. A projection end of a light guide fiber bundle 4 is placed so as to lighten its subject.

A circuit substrate 23 is electrically connected to the solid image sensor 222 and placed in an operating portion 3. A drive circuit of the solid image sensor 222, a process circuit of a video signal, a video signal transmitting circuit, and the like are mounted on the circuit substrate 23. The video signal transmitting circuit mounted on the circuit substrate 23 converts a video signal of an endoscopic observation picture taken by the solid image sensor 22 to a radio signal and transmits (oscillates) it from a transmitting antenna 21. The circuit substrate 23 used in the second embodiment has the similar structure and function to those of the circuit substrate 23 used in the first embodiment. Therefore, the detailed description of the structure and function of the circuit substrate 23 is omitted.

As shown in FIG. 7, the power for driving the solid image sensor 222 and the circuits mounted on the circuit substrate 23 is supplied from a power electric cell 13 of a light source unit 10 through an electric wire 9 wired in the operating portion 3 to the circuit substrate 23.

A contact 91 is provided for a joint portion of the light source unit 10 in relation to the operating portion 3. When the light source unit 10 is coupled to the operating portion 3, the power electric cell 13 and the electric wire 9 are connected to each other through a switch 14.

As a result, by operating a switch ring 11 turning to close the switch 14, a light source lamp 12 is turned on and simultaneously the power for operating the solid image sensor 222 and the circuits on the circuit substrate 23 is supplied all from the power electric cell 13 of the light source unit 10. Further, any cables are not extended out of the operating portion 3, and the video signal of the endoscopic observation picture is transmitted from the transmitting antenna 21 by radio.

Radio wave of the video signal thus transmitted from the transmitting antenna 21 is, as shown in FIG. 8, received by a receiver 30 provided with a receiving antenna 31, and the endoscopic observation picture is projected onto a television monitor 40 connected to its receiver 30.

Third Embodiment

Figure 9:
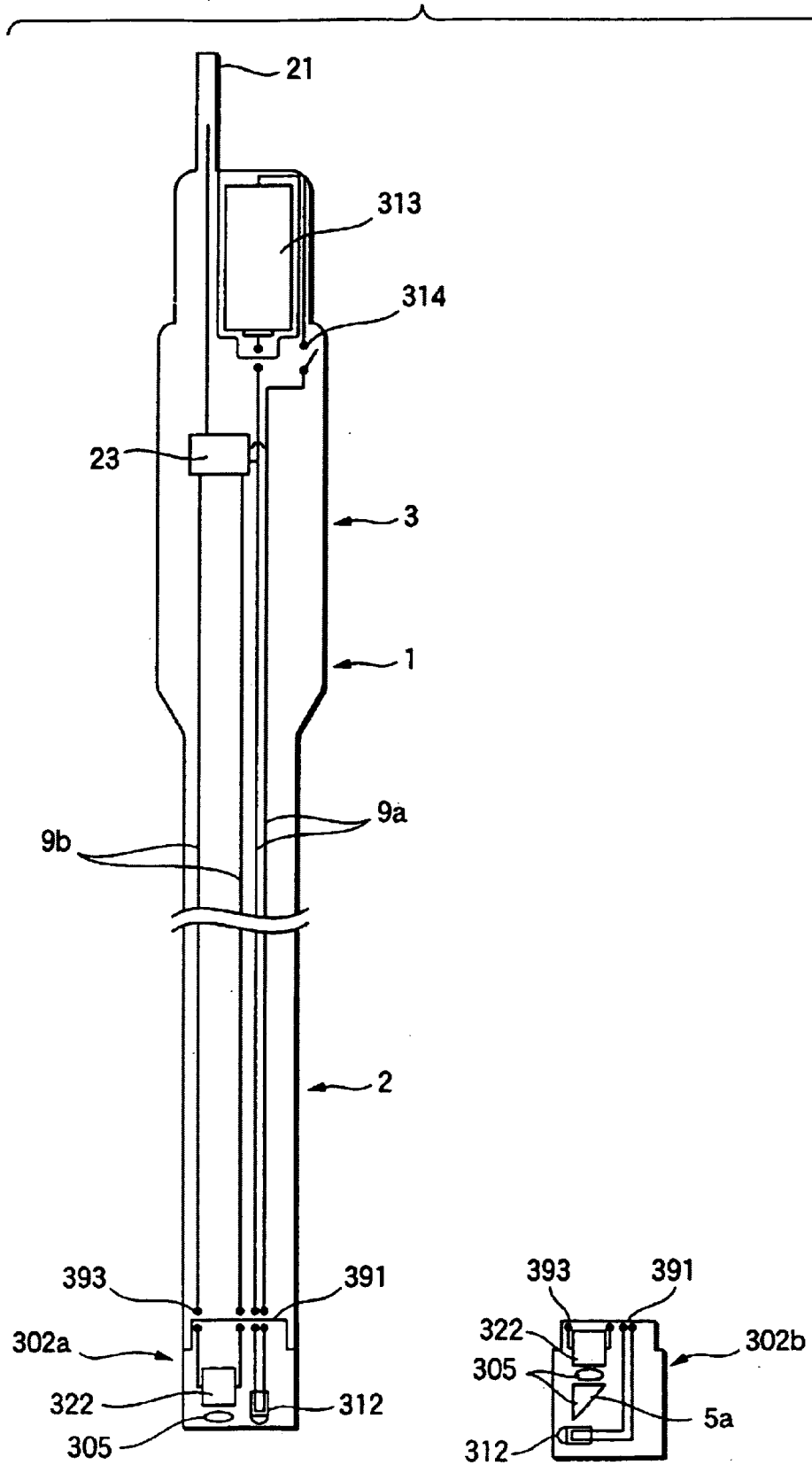
FIG. 9 is a schematic diagram showing the inside structure of a portable endoscope according to a third embodiment of the invention.
Figure 10:
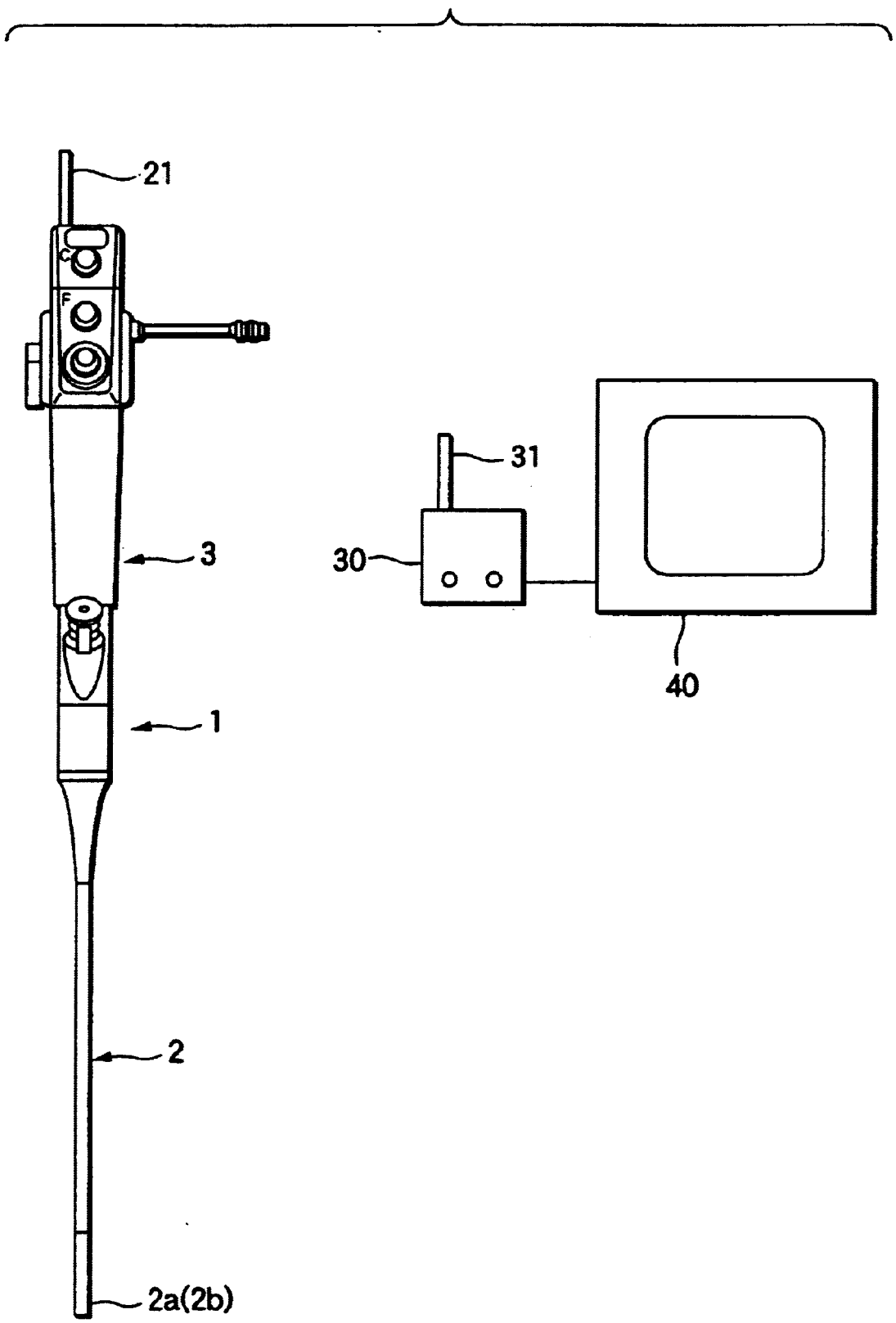
FIG. 10 is an external front view of the portable endoscope according to the third embodiment of the invention.

FIGS. 9 and 10 show a third embodiment of a portable endoscope according to the invention. Since the same component parts as those in the first embodiment are denoted by the same reference numerals, their detailed description is omitted.

An inserted portion 2 of a portable endoscope 1 is covered with a flexible tube, and a distal end body 302*a* (302*b*) that includes an objective optical system 5 is provided at the distal end of the inserted portion 2 detachably and exchangeably.

Figure 11:
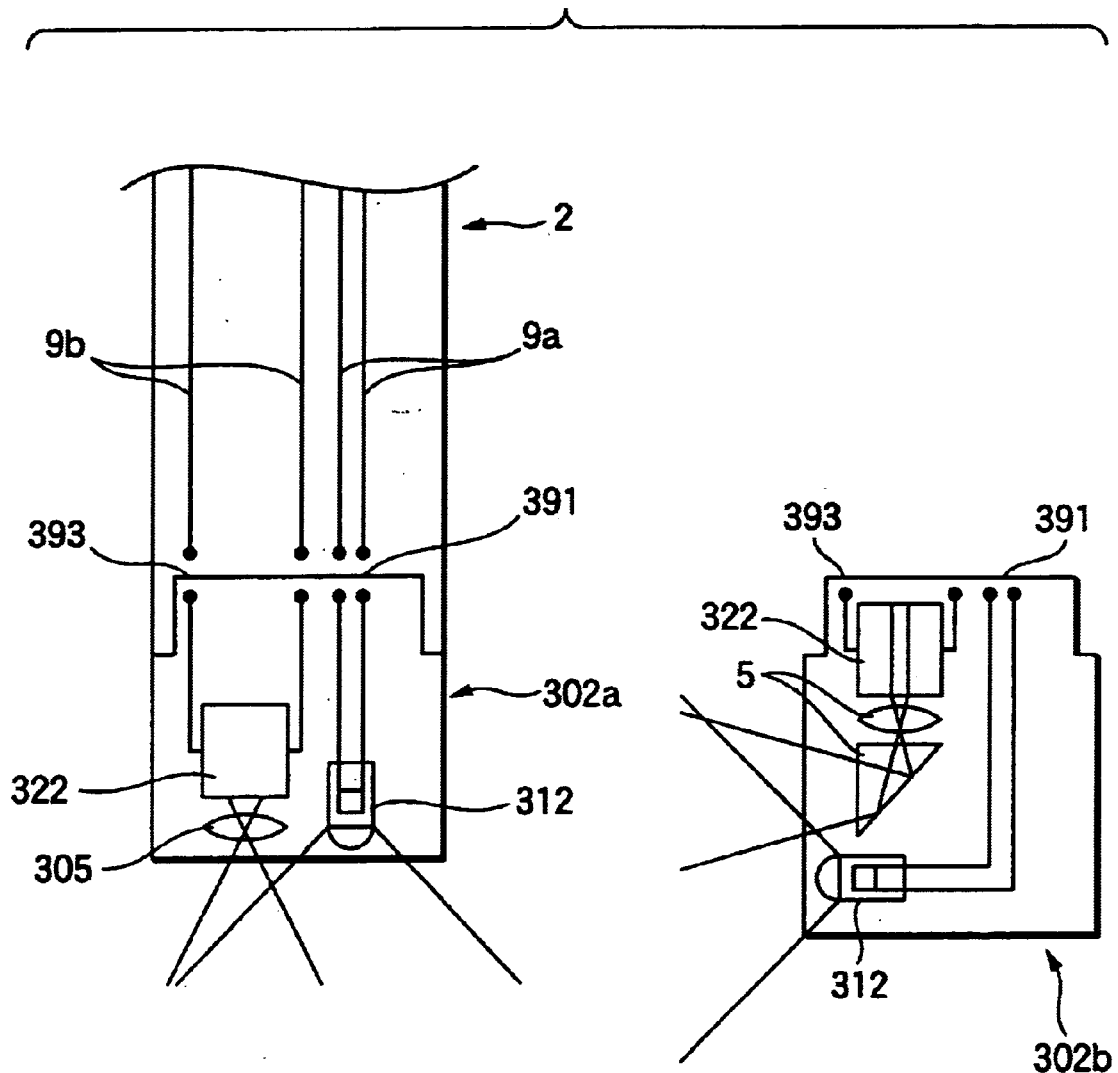
FIG. 11 is a schematically enlarged diagram showing the structure of a distal end portion of an inserted portion of the portable endoscope according to the third embodiment of the invention.

In this embodiment, as shown in an enlarged view of FIG. 11, as the distal end bodies 302*a*, 302*b*, a distal end body 302*a* for forward view and a distal end body 302*b* or side view are prepared. In FIGS. 9 and 11, the distal end body 302*a* for forward view is attached.

A lighting light source 312 for lightening a subject, for example, a light source comprising a white light emitting diode, a solid image sensor 322 for taking an endoscopic observation picture of its subject, and an objective optical system 305 for imaging an image of the subject on an image surface of the solid image sensor 322 are placed in each of the distal end bodies 302*a*, 302*b*.

A rectangular roof prism 5*a* is included in the objective optical system 305 of the distal end body 302*b* for side view. However, instead of the rectangular roof prism 5*a*, a simple rectangular prism may be used, and right and left reversal of the image may be processed by electronic signals.

Each of the distal end bodies 302*a*, 302*b* fits to the distal end portion of the inserted portion 2, and is coupled and fixed to it by a fixing ring (not shown) or the like. A power-line connecting contact 391 and a signal-line connecting contact 393 are placed at its coupling portion. The distal end body is electrically connected to the inserted portion 2 when they are mechanically coupled to each other.

On the distal end body 302*a* (302*b*) side, the lighting light source 312 is connected to the power-line connecting contact 391, and the solid image sensor 322 is connected to the signal-line connecting contact 393. On the inserted portion 2 side, a power transmitting line 9*a* is connected to the power-line connecting contact 391, a signal transmitting line 9*b* is connected and to the signal-line connecting contact 393.

In an operating portion 3 coupled to the base end of the inserted portion 2, a power electric cell 313 is included detachably and exchangeably, and the power electric cell 313 is connected to the power-transmitting line 9*a* through a switch 314.

A drive circuit of the solid image sensor 22, a process circuit of a video signal, a video signal transmitting circuit, and the like are mounted on a circuit substrate 23 connected to the signal transmitting line 9*b* in the operating portion 3, and the power transmitting line 9*a* is connected to the signal transmitting line 9*b*. Reference numeral 21 is a transmitting antenna connected to the circuit substrate 23. The video signal transmitting circuit mounted on the circuit substrate 23 converts a video signal of the endoscopic observation picture taken by the solid image sensor 322 into a radio signal and transmits (oscillates) the radio signal from the transmitting antenna 21. The circuit substrate 23 used in the third embodiment has the structure and function similar to those of the circuit substrate 23 used in the first embodiment.

Therefore, the detailed description of the structure and function of the circuit substrate 23 is omitted.

As shown in FIG. 9, when the switch 314 provided for the operating portion 3 is turned on, the power electric cell 313 is connected to the power transmitting line 9a, the lighting power is supplied to the lighting light source 312, and simultaneously the power for operating the solid image sensor 322 and the circuits mounted on the circuit substrate 23 is supplied to the circuit substrate 23.

The video signal of the endoscopic observation picture taken by the solid image sensor 322 is processed by the circuit substrate 23 through the signal transmitting line 9b and sent from the transmitting antenna 21 as a radio signal. Thus, any cables are not extended out of the operating portion 3, and the video signal of the endoscopic observation picture is transmitted from the transmitting antenna 21 by radio.

Radio wave of the video signal transmitted from the transmitting antenna 21 is, as shown in FIG. 10, received by a receiver 30 provided with a receiving antenna 31, and the endoscopic observation picture is projected onto a television monitor 40 connected to its receiver 30.

Further, the radio transmission and reception of the invention may be performed by communication using infrared rays instead of using radio waves. Particularly, in case that the influence of electromagnetic waves between the endoscope and another medical device in the medical spot is taken into consideration, the infrared communication is easier in design of communication algorithm than the radio wave communication.

According to the invention, the power for driving the circuits of the radio transmission television camera attached to the eyepiece portion of the portable endoscope is supplied from the power source of the light source unit directly coupled to the operating portion, whereby it is not necessary to extend out the cable for transmitting the video signal. Therefore, while the good operational efficiency of the portable endoscope is kept, the endoscopic observation picture can be taken and observed on the reception device side.

Further, since it is not necessary to place the power source in the radio transmission television camera, the television camera can have the lightweight structure, so that the operational efficiency is good also in this point.

What is claimed is:

1. A television device of a portable endoscope comprising:
    an endoscope including an insertion portion and an operating portion coupled to a base end of the insertion portion;
    a radio transmission television camera detachably coupled to the operating portion for obtaining an image of the subject through the insertion portion and radioing the image as a video signal, the radio transmission television camera provided in the endoscope; and
    a light source unit detachably coupled to the operating portion and separated from the radio transmission television camera, the light source unit including a light source for illuminating the subject through the insertion portion and a power source that supplies power for both the light source and the radio transmission television camera.

2. The television device according to claim 1, further comprising an eyepiece portion provided at the operating portion, the image of the subject being projected through said eyepiece portion, and the radio transmission camera being coupled to said eyepiece portion.

3. The television device according to claim 2, wherein a wire for electrically connecting the radio transmission television camera to the power source is provided in the operating portion and the eyepiece portion.

4. The television device according to claim 2, wherein a wire for electrically connecting the radio transmission television camera unit to the power source is outside the operating portion and the eyepiece portion.

5. The television device according to claim 1, wherein a light source unit including the light source and the power source is detachably coupled to the operating portion.

6. The television device according to claim 1, wherein the radio transmission television camera includes a solid state image sensor for capturing an image of the subject and a circuit including at least one of a drive circuit for driving the solid state image sensor, a process circuit for processing the video signal and a transmitting circuit for transmitting the video signal.

7. The television device according to claim 6, wherein the solid state image sensor and the circuit are integrally formed.

8. The television device according to claim 1, wherein the video signal is transmitted by at least one of infrared rays and radio waves.

9. The television device according to claim 1, wherein a transmitting antenna is provided at the operating portion.

10. The television device according to claim 1, wherein the power source is a power electric cell.

11. The television device according to claim 1, further comprising:
    a distal end portion that includes a solid state image sensor for capturing a subject and a light source for illuminating the subject, the distal end portion being detachably mounted to a distal end of the insertion portion; and
    a radio transmission unit of the television camera for radioing the image from the solid state image sensor as a video signal.

12. The television device according to claim 11, wherein the radio transmission unit includes a circuit including at least one of a drive circuit for driving the solid state image sensor, a process circuit for processing the video signal and a transmitting circuit for transmitting the video signal.

13. The television device according to claim 12, wherein the solid image sensor and the circuit are integrally formed in the distal end portion.

14. The television device according to claim 12, wherein the distal end portion, including the solid image sensor and the light source, is exchangeable for another type of distal end portion that obtains the image of the subject from a different direction.

15. The television device according to claim 11, wherein the power source is detachably provided in the operating portion.

16. The television device according to claim 11, wherein the video signal is transmitted by at least one of infrared rays and radio waves.

17. The television device according to claim 11, wherein a transmitting antenna is provided at the operating portion.

18. The television device according to claim 11, wherein the power source is a power electric cell.

19. A television device of a portable endoscope comprising:
    an endoscope including an insertion portion and an operating portion coupled to a base end of the insertion portion;
    a radio transmission television camera detachably coupled to the operating portion for obtaining an image of a subject through the insertion portion and radioing the image as a video signal;

a light source unit detachably coupled to the operating portion and separated from the radio transmission television camera, the light source unit including a light source for illuminating the subject through the insertion portion and a power source that supplies power for both the light source and the radio transmission television camera.

20. The television device according to claim 19, wherein the radio transmission television camera includes a solid state image sensor for capturing an image of the subject and a circuit including at least one of a drive circuit for driving the solid state image sensor, a process circuit for processing the video signal and a transmitting circuit for transmitting the video signal.

21. The television device according to claim 20, wherein the solid image sensor and the circuit are integrally formed.

22. The television device according to claim 19, wherein the video signal is transmitted by at least one of infrared rays and radio waves.

23. The television device according to claim 19, wherein a transmitting antenna is provided at the operating portion.

24. The television device according to claim 19, wherein the power source is a power electric cell.

* * * * *